US006984726B1

(12) United States Patent
Ferreira et al.

(10) Patent No.: US 6,984,726 B1
(45) Date of Patent: Jan. 10, 2006

(54) **RECOMBINANT MAJOR ALLERGEN OF THE POLLEN OF *ARTEMISIA VULGARIS* (MUGWORT)**

(75) Inventors: Fatima Ferreira, Anthering (AT); Klaus Richter, Anif (AT); Martin Himly, Villach (AT); Edwin Engel, Kammern (AT); Christof Ebner, Brunn Am Gebirge (AT); Michael Breitenbach, Salzburg (AT); Dietrich Kraft, Vienna (AT)

(73) Assignee: BIOMAY Produktions- und Handels-Aktiengesellschaft, Vienna (AT)

( * ) Notice: Subject to any disclaimer, the term of this patent is extended or adjusted under 35 U.S.C. 154(b) by 0 days.

(21) Appl. No.: 09/647,234

(22) PCT Filed: Mar. 25, 1999

(86) PCT No.: PCT/AT99/00081

§ 371 (c)(1),
(2), (4) Date: Apr. 25, 2001

(87) PCT Pub. No.: WO99/49045

PCT Pub. Date: Sep. 30, 1999

(30) Foreign Application Priority Data

Mar. 26, 1998 (AT) ...................................... 539/98

(51) Int. Cl.
*C07H 21/04* (2006.01)

(52) U.S. Cl. ................. 536/23.6; 435/320.1; 435/69.1; 435/419; 435/325; 435/252.33; 435/255.5; 800/278; 800/317.3

(58) Field of Classification Search ............... 536/23.5, 536/23.6; 800/278, 317.3; 435/419, 325, 435/252.33, 255.5, 320.1, 69.1
See application file for complete search history.

(56) References Cited

FOREIGN PATENT DOCUMENTS

WO WO 97/05258 2/1997

OTHER PUBLICATIONS

Hirschwehr, Journal of Allergy and Clinical Immunology, 1998. 101:196-206.*
Charpin et al., 1974, Atlas of European Allergenic Pollen.
Cornillion et al., 1972, Estivo-autumnal pollinosis, Rev. Franc. Allergol. 12:131-135 (English abstract).
De La Hoz, 1990, Purification of Art v I, a relevant allergen of *Artemisia vulagris* pollen, Mol. Immunol. 27(7):651-657.
Domon et al., 1990, Nucleotide sequence of two anther-specific cDNAs from sunflower (*Helianthus annuus* L), Plant Mol. Biol. 15:643-646.
Hirschwehr et al., 1998, Identification of common allergenic structures in mugwort and ragweed pollen, J. Allergy Clin. Immunol. 101(2 Pt 1):196-206.
Matthiesen et al., In: Allergenic pollen and pollinosis in Europe, D'Amato et al., eds.; 1990, pp. 33-44.
Nielson et al., 1997, Identification of prokaryotic and eukaryotic signal peptide and prediction of their cleavage sites, Protein Eng. 10:1-6.
Spieksma et al., 1980, City Spore Concentration in the European Economic Community (EEC), Clinical Allergy 10:319-329.

* cited by examiner

*Primary Examiner*—Patrick J. Nolan
(74) *Attorney, Agent, or Firm*—Henry M. Feiereisen; Ursula B. Day

(57) ABSTRACT

The invention relates to DNA molecules which code for the allergen Art v 1 or isoforms thereof, the sequence of the allergen, a method for the production of an Art v 1 molecule, a vector and a transformed host cell.

24 Claims, 9 Drawing Sheets

Fig. 1

```
1                     5                          10                      15                      20
Met Ala Lys Cys Ser Tyr Val Phe Cys Ala Val Leu Leu Ile Phe Ile Val Ala Ile Gly
ATG GCA AAG TGT TCA TAT GTT TTC TGT GCG GTT CTT CTG ATT TTC ATA GTT GCT ATC GGA
1           9           18          27          36          45          54

25                      30                      35                      40
Glu Met Glu Ala Ala Gly Ser Lys Leu Cys Glu Lys Thr Ser Lys Thr Tyr Ser Gly Lys
GAA ATG GAG GCC GCT GGT TCA AAG TTG TGT GAA AAG ACA AGC AAG ACG TAT TCG GGT AAG
63          72          81          90          99          108         117

45                      50                      55                      60
Cys Asp Asn Lys Lys Cys Asp Lys Lys Cys Ile Glu Trp Glu Lys Ala Gln His Gly Ala
TGC GAC AAC AAG AAA TGT GAC AAA AAG TGT ATA GAG TGG GAG AAA GCG CAA CAT GGT GCT
126         135         144         153         162         171         180

65                      70                      75                      80
Cys His Lys Arg Glu Ala Gly Lys Glu Ser Cys Phe Cys Tyr Phe Asp Cys Ser Lys Ser
TGT CAC AAG AGA GAA GCC GGC AAA GAA AGT TGC TTT TGC TAC TTT GAC TGT TCC AAA TCG
            189         198         207         216         225         234

85                      90                      95                      100
Pro Pro Gly Ala Thr Pro Ala Pro Pro Gly Ala Ala Pro Pro Pro Ala Ala Gly Gly Ser
CCT CCT GGA GCA ACA CCA GCG CCT CCT GGT GCA GCT CCT CCC CCA GCT GCT GGC GGC TCT
243         252         261         270         279         288         297

105                     110                     115                     120
Pro Ser Pro Pro Ala Asp Gly Gly Ser Pro Pro Pro Ala Asp Gly Gly Ser Pro Pro
CCG TCA CCT CCC GCT GAT GGT GGC TCA CCA CCT CCT CCA GCT GAT GGT GGA TCT CCT CCT
306         315         324         333         342         351         360

125                     130
Val Asp Gly Gly Ser Pro Pro Pro Ser Thr His *
GTA GAT GGT GGC TCT CCA CCT CCT CCG TCC ACT CAC TAA
            369         378         387         396
```

Fig. 2

```
1                  5                      10                         15                      20
Met Ala Arg Cys Ser Tyr Val Phe Cys Ala Val Leu Leu Ile Phe Val Leu Ala Ile Gly
ATG GCG AGG TGT TCA TAT GTT TTC TGC GCG GTT CTT CTG ATT TTC GTA CTT GCT ATC GGA
         9               18              27         36              45         54

25                     30                    35                      40
Glu Ile Glu Ala Ala Gly Ser Lys Leu Cys Glu Lys Thr Ser Lys Thr Tyr Ser Gly Lys
GAA ATT GAG GCC GCT GGT TCA AAG CTG TGT GAA AAG ACA AGC AAG ACG TAT TCG GGT AAG
63              72              81         90              99        108         117

45                      50                       55                     60
Cys Asp Asn Lys Lys Cys Asp Lys Lys Cys Ile Glu Trp Glu Lys Ala Gln His Gly Ala
TGC GAC AAC AAG AAA TGT GAC AAA AAG TGT ATA GAA TGG GAG AAA GCA CAA CAT GGT GCT
      126             135             144         153             162         171             180

65                      70                      75                     80
Cys His Lys Arg Glu Ala Gly Lys Glu Ser Cys Phe Cys Tyr Phe Asp Cys Ser Lys Ser
TGT CAC AAG AGA GAA GCC GGT AAA GAA AGT TGC TTT TGC TAC TTT GAC TGT TCC AAA TCG
         189             198             207         216             225         234

85                      90                       95                      100
Pro Pro Gly Ala Thr Pro Ala Pro Pro Gly Ala Ser Pro Pro Pro Ala Ala Gly Gly Ser
CCT CCT GGA GCG ACA CCA GCG CCT CCT GGA GCA TCT CCT CCC CCA GCT GCT GGC GGC TCT
243             252             261         270             279         288             297

105                     110                   115                     120
Pro Pro Pro Pro Ala Asp Gly Gly Ser Pro Pro Pro Ala Asp Gly Gly Ser Pro Pro
CCA CCA CCT CCC GCC GAT GGT GGC TCA CCA CCT CCT CCA GCT GAT GGT GGA TCT CCT CCT
         306             315             324         333             342         351             360

125                    130
Ala Asp Gly Gly Ser Pro Pro Pro Ser Ala His *
GCC GAT GGT GGC TCT CCA CCT CCT CCG TCC GCT CAC TAA
         369             378             387         396
```

Fig. 3

```
1               5                  10                  15                  20
Met Ala Lys Cys Ser Tyr Val Phe Cys Ala Val Leu Leu Ile Phe Ile Leu Ala Ile Gly
ATG GCA AAG TGT TCA TAT GTT TTC TGT GCG GTT CTT CTG ATT TTC ATA CTT GCT ATC GGA
         9          18          27          36          45          54

25                  30                  35                  40
Glu Ile Glu Ala Ala Gly Ser Lys Leu Cys Glu Lys Thr Ser Lys Thr Tyr Ser Gly Lys
GAA ATA GAG GCC GCT GGT TCA AAG CTG TGT GAA AAG ACA AGC AAG ACG TAT TCA GGT AAG
 63          72          81          90          99         108         117

45                  50                  55                  60
Cys Asp Asn Lys Lys Cys Asp Lys Lys Cys Ile Glu Trp Glu Lys Ala Gln His Gly Ala
TGC GAC AAC AAG AAA TGT GAC AAA AAG TGT ATA GAA TGG GAG AAA GCA CAA CAT GGT GCT
            126         135         144         153         162         171         180

65                  70                  75                  80
Cys His Lys Arg Glu Ala Gly Lys Glu Ser Cys Phe Cys Tyr Phe Asp Cys Ser Lys Ser
TGT CAC AAG AGA GAA GCC GGT AAA GAA AGT TGC TTT TGC TAC TTT GAC TGT TCC AAA TCG
            189         198         207         216         225         234

85                  90                  95                 100
Pro Pro Gly Ala Thr Pro Ala Pro Pro Gly Ala Ser Pro Pro Pro Ala Ala Gly Gly Ser
CCT CCT GGA GCG ACA CCA GCG CCT CCT GGA GCA TCT CCT CCC CCA GCT GCT GGC GGC TCT 243
252         261         270         279         288         297

105                 110                 115                 120
Pro Pro Pro Pro Ala Asp Gly Gly Ser Pro Pro Pro Pro Ala Asp Gly Gly Ser Pro Pro
CCA CCA CCT CCC GCC GAT GGT GGC TCA CCA CCT CCT CCA GCT GAT GGT GGA TCT CCT CCT
306         315         324         333         342         351         360

125                 130
Ala Asp Gly Gly Ser Pro Pro Pro Pro Ser Ala His  *
GCC GAT GGT GGC TCT CCA CCT CCT CCG TCC GCT CAC TAA
            369         378         387         396
```

Fig. 4

```
    ATGGCAAAGTGTTCATATGTTTTCTGTGCGGTTCTTCTGA                  Consensus
             10        20        30        40
1   ATGGCAAAGTGTTCATATGTTTTCTGTGCGGTTCTTCTGA                  Art v 1a
1   ATGGCG A G T GTTCATATGTTTTCTGCGCGGTT T TCTGA              Art v 1b
1   ATGGCAAAGTGTTCATATGTTTTCTGTGCGGTTCTTCTGA                  Art v 1c TTTTCATACTTGCTATCGGAGAAATXGAGGCCGCTGGTTC                  Consensus
             50        60        70        80
41  TTTTCATAGT T G CTATCGGAGAAATGGAGGCC G CTGGTTC             Art v 1a
41  TTTTCG T A CTTGCTATCGGAGAAATTGAGGCC G CTGGTTC             Art v 1b
41  TTTTCATACTTGCTATCGGAGAAATAGAGGCC G CTGGTTC                Art v 1c AAAGCTGTGTGAAAAGACAAGCAAGACGTATTCGGGTAAG                  Consensus
             90       100       110       120
81  AAAGT T G TGTGAAAAGACAAGCAAGACGTATTCGGGTAAG               Art v 1a
81  AAAGCTGTGTGAAAAGACAAGCAAGACGTATTCGGGTAAG                  Art v 1b
81  AAAGCTGTGTGAAAAGACAAGCAAGACGTATTCAGGTAAG        □         Art v 1c TGCGACAACAAGAAATGTGACAAAAAGTGTATAGAATGGG                  Consensus
            130       140       150       160
121 TGCGACAACAAGAAATGTGACAAAAAGTGTATAGAGTGGG        □         Art v 1a
121 TGCGACAACAAGAAATGTGACAAAAAGTGTATAGAATGGG                  Art v 1b
121 TGCGACAACAAGAAATGTGACAAAAAGTGTATAGAATGGG                  Art v 1c AGAAAGCACAACATGGTGCTTGTCACAAGAGAGAAGCCGG                  Consensus
            170       180       190       200
161 AGAAAGCG C A ACATGGTGCTTGTCACAAGAGAGAAGCCGG                Art v 1a
161 AGAAAGCACAACATGGTGCTTGTCACAAGAGAGAAGCCGG                  Art v 1b
161 AGAAAGCACAACATGGTGCTTGTCACAAGAGAGAAGCCGG                  Art v 1c TAAAGAAAGTTGCTTTTGCTACTTTGACTGTTCCAAATCG                  Consensus
            210       220       230       240
201 C AAAGAAAGTTGCTTTTGCTACTTTGACTGTTCCAAATCG                 Art v 1a
201 TAAAGAAAGTTGCTTTTGCTACTTTGACTGTTCCAAATCG                  Art v 1b
201 TAAAGAAAGTTGCTTTTGCTACTTTGACTGTTCCAAATCG                  Art v 1c CCTCCTGGAGCGACACCAGCGCCTCCTGGAGCATCTCCTC                  Consensus
            250       260       270       280
241 CCTCCTGGAGCAAC A CCAGCGCCTCCTGGTGCAGCTC C C   □            Art v 1a
241 CCTCCTGGAGCGACACCAGCGCCTCCTGGAGCATCTCCTC                  Art v 1b
241 CCTCCTGGAGCGACACCAGCGCCTCCTGGAGCATCTCCTC                  Art v 1c CCCCAGCTGCTGGCGGCTCTCCACCACCTCCCGCCGATGG                  Consensus
            290       300       310       320
281 CCCCAGCTGCTGGCGGCTCTCCGTCACC TCC CGCTGATGG    □            Art v 1a
281 CCCCAGCTGCTGGCGGCTCTCCACCACCTCCCGCCGATGG                  Art v 1b
281 CCCCAGCTGCTGGCGGCTCTCCACCACCTCCCGCCGATGG                  Art v 1c
```

Continuation Fig. 4

```
        TGGCTCACCACCTCCTCCAGCTGATGGTGGATCTCCTCCT                      Consensus
                330           340           350          360
321     TGGCTCACCACCTCCTCCAGCTGATGGTGGATCTCCTCCT                      Art v 1
321     TGGCTCACCACCTCCTCCAGCTGATGGTGGATCTCCTCCT                      Art v 1
321     TGGCTCACCACCTCCTCCAGCTGATGGTGGATCTCCTCCT                      Art v 1

GCCGATGGTGGCTCTCCACCTCCTCCGTCCGCTCACTAA                       Consensus
                 370           380           390
361     G TAG ATGGTGGCTCTCCACCTCCTCCGTCCACTCACTAA                     Art v 1a
361     GCCGATGGTGGCTCTCCACCTCCTCCGTCCGCTCACTAA                       Art v 1b
361     GCCGATGGTGGCTCTCCACCTCCTCCGTCCGCTCACTAA                       Art v 1c
```

Fig. 5

| | Consensus |
|---|---|
| MAKCSYVFCAVLLIFILAIGEIEAAGSKLC | |
| 10  20  30 | |
| 1  MAKCSYVFCAVLLIFIVAIGE M E AAGSK L C | Art v 1a |
| 1  MA R CSYVFCAVLLIFVLAIG E EAAGSKLC | Art v 1b |
| 1  MAKCSYVFCAVLLIFILAIGEIEAAGSKLC | Art v 1c |

| | Consensus |
|---|---|
| EKTSKTYSGKCDNKKCDKKCIEWEKAQHGA | |
| 40  50  60 | |
| 31  EKTSKTYSGKCDNKKCDKKCIEWEKAQHGA | Art v 1a |
| 31  EKTSKTYSGKCDNKKCDKKCIEWEKAQHGA | Art v 1b |
| 31  EKTSKTYSGKCDNKKCDKKCIEWEKAQHGA | Art v 1c |

| | Consensus |
|---|---|
| CHKREAGKESCFCYFDCSKSPPGATPAPPG | |
| 70  80  90 | |
| 61  CHKREAGKESCFCYFDCSKSPPGATPAPPG | Art v 1a |
| 61  CHKREAGKESCFCYFDCSKSPPGATPAPPG | Art v 1b |
| 61  CHKREAGKESCFCYFDCSKSPPGATPAPPG | Art v 1c |

| | Consensus |
|---|---|
| ASPPPAAGGSPPPPADGGSPPPPADGGSPP | |
| 100  110  120 | |
| 91  A A PPPAAGGSPSPPA D GGSPPPPADGGSPP | Art v 1a |
| 91  ASPPPAAGGSPPPPADGGSPPPPADGGSPP | Art v 1b |
| 91  ASPPPAAGGSPPPPADGGSPPPPADGGSPP | Art v 1c |

| | Consensus |
|---|---|
| ADGGSPPPPSAH | |
| 130 | |
| 121  V DGGSPPPPSTH | Art v 1a |
| 121  ADGGSPPPPSAH | Art v 1b |
| 121  ADGGSPPPPSAH | Art v 1c |

A
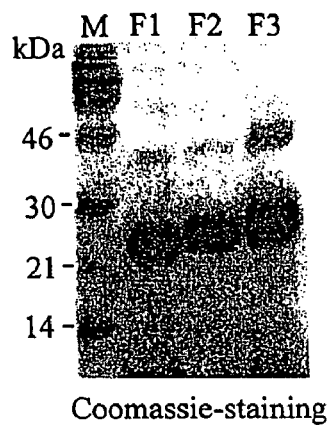
Coomassie-staining
B
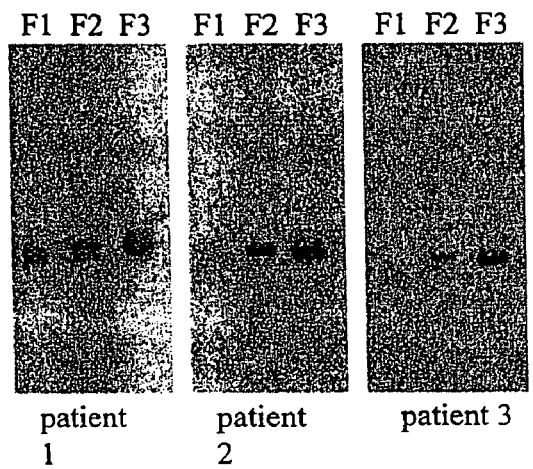
C
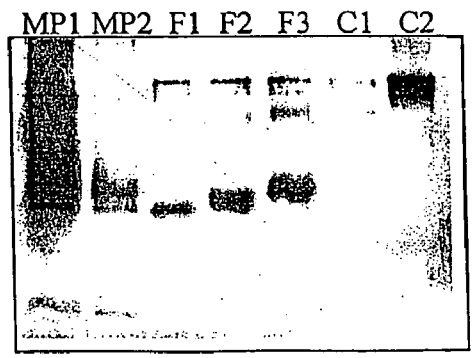
Sugar detection
Fig. 6

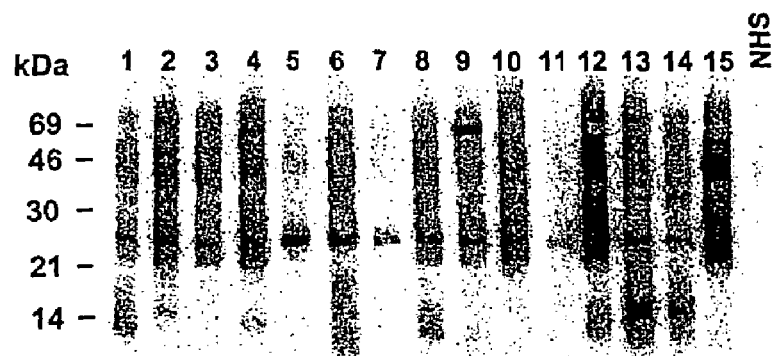
MUGWORT POLLEN
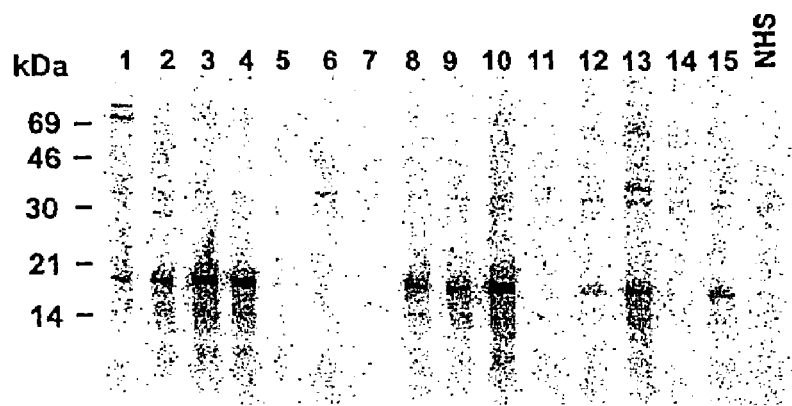
rArt v 1a
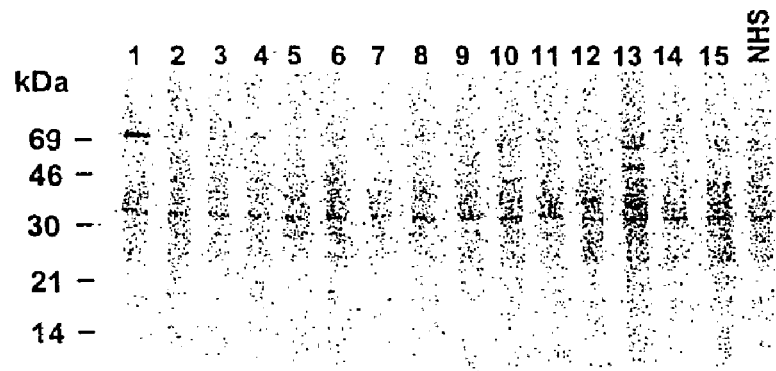
CONTROL
Fig. 8

RECOMBINANT MAJOR ALLERGEN OF THE POLLEN OF *ARTEMISIA VULGARIS* (MUGWORT)

The present application is a 35 USC §371 application of PCT/AT99/00081 filed Mar. 25, 1999, which was published on Sep. 30, 1999 as WO 99/49045, which claims priority benefits of Austrian Application A 539/98, filed Mar. 26, 1998.

BACKGROUND OF THE INVENTION

The present invention relates to recombinant DNA molecules coding for the allergen Art v 1, to a method for preparation of a Art v 1 molecule, and to a vector and a transformed host cell.

Pollen of mugwort is one of the main causes of allergies in Europe in late summer (1,2). Among all patients suffering from pollinosis, the incidence of allergic disease caused by mugwort pollen is between 10 and 14% (2,3). Immunoblots of total protein from extracts of mugwort pollen show that the patients' IgE recognize a major allergen of 27–29 kDa, which is therefore called Art v 1. Over 95% of all patients that are allergic against mugwort pollen, recognize Art v 1 in an IgE immunoblot. Such blots will be called "patient blots" from here on. Several other proteins in mugwort pollen extract migrate at the same apparent Mr of 27–29 kDa. It was therefore difficult to isolate a cDNA clone and proof that it codes for Art v 1.

Object of the invention is to provide a recombinant DNA molecule that codes for the allergen of pollen from *Artemisia vulgaris*.

SUMMARY OF THE INVENTION

According to the invention, this is achieved in a way that a recombinant DNA molecule is created which codes for the allergen Art v 1a, which has the sequence shown in SEQ ID NO:2. This means that the major allergen of *Artemisia vulgaris* was found and made accessible for diagnose and therapy, respectively. Those DNA molecules are characterized by the nucleotide sequence according to SEQ ID NO:1. Those molecules can as well be derived from amino acid sequence according to SEQ ID NO:2 through degeneration of the genetic code. Preferentially, the molecules according to the invention can have more than 60% sequence identity with SEQ ID NO:1. In addition, the recombinant DNA molecule according to the invention can code for the amino acid sequences of the isoforms Art v 1b and Art v 1c, which have the sequences shown in SEQ ID NO:4 and 6. Those recombinant DNA molecules can have the nucleotide sequences shown in SEQ ID NO:3 and 5. The recombinant DNA molecules according to the invention can hybridize with the sequence shown in SEQ ID NO:1 and remain bound through hybridization under stringent washing conditions. The same is true for the sequences shown in SEQ ID NO:3 and 5. Stringent hybridization conditions are for example 1M NaCl in H$_2$0 at 60° C. and stringent washing conditions are for example 2 times washing at 50° C. in 5×SSPE and 0.1% SDS (1×SSPE is 0.18 M NaCl, 0.01M sodium phosphate pH 7.4, 1 mM EDTA).

BRIEF DESCRIPTION OF THE DRAWINGS

FIG. 1 shows the nucleotide sequence and derived amino acid sequence of Art v 1a as identified in SEQ ID No. 2, wherein the derived amino acid begins with the start methionine. The N-terminal signal sequence predicted by computer analysis is seen in italics; the N-terminal amino acid sequence of the natural allergen determined through Edman degradation is seen as underlined.

FIG. 2 shows the nucleotide sequence and derivative amino acid sequence of Art v 1 b. as identified in SEQ ID No. 4, wherein the derived amino acid sequence starts with the initiating methionine. The N-terminal signal sequence as predicted by computer analysis is seen in italics; the N-terminal amino acid sequence of the natural allergen determined through Edman degradation is seen as underlined.

FIG. 3 shows the shows the nucleotide sequence and derivative amino acid sequence of Art v 1c. as identified in SEQ ID No. 6, wherein the derived amino acid sequence starts with the initiating methionine. N-terminal signal sequence predicted by computer analysis is in italics; N-terminal amino acid sequence of the natural allergen as determined by Edman degradation is underlined.

FIG. 4 shows a comparison of the nucleotide sequence of the open reading frame of Art v 1a, Art v 1b and Art v 1c. Nucleotides not identical in all three sequences are boxed.

FIG. 5 shows a comparison of the derived amino acids sequence of Art v 1a, Art v 1b and Art v 1c. Amino acids identical in all three sequences are boxed.

FIG. 6 shows a chracterization of the purified natural allergen Art v1. part A; Coomassie-staining of three fractions containing Art v 1 (F 1, F2 and F3). These fractions were tested for their IgE binding with sera from three mugwort pollen-allergic patients (panel B). Panel C: DIG glycan/protein staining from mugwort pollen extract (lanes MP1 and MP 2), and of purified Art v 1 fractions (lanes F1, F2 and F3). C1, negative control (recombinant creatinase); C2, positive control (fetuin).

FIG. 8 shows the IgE immunoblot of recombinant Art v 1a (rArtv 1 a). Sera form 15 mugwort-allergic patients were tested for their IgE binding with mugwort pollen extract and rArt v 1a which was expresed in *E. coli* BL 21. Bacterial lysate of *E. coli* was used for the control which contained the expression vector pMW172 without insert. NHS: normal human serum.

Figure 7:
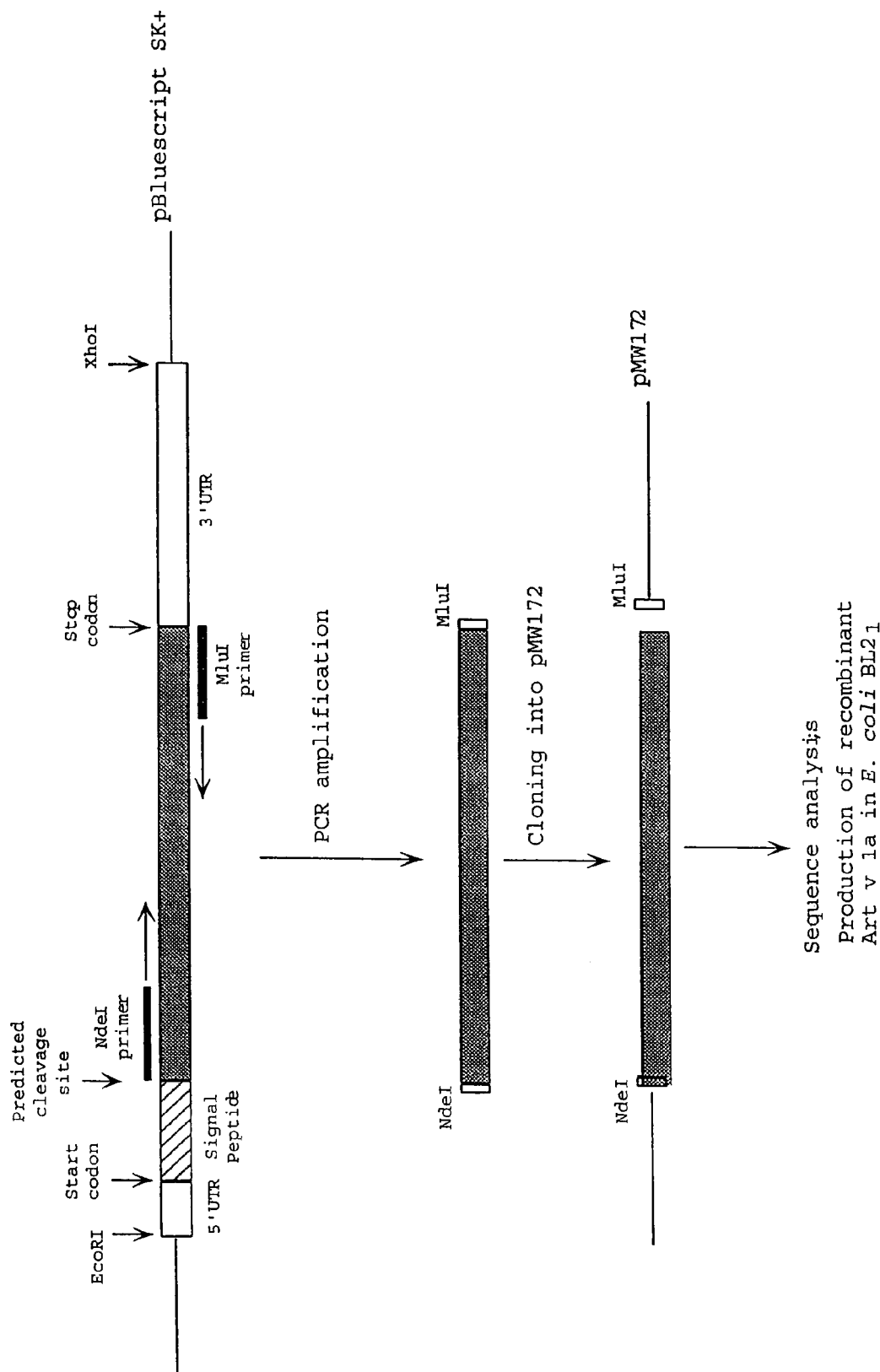
FIG. 7 shows construction of the expressed plasmid for Art v 1a. The Art v 1a cDNA part corresponding to the mature form of the protein was expressed in *E. coli* as a non fusion protein.

A method according to the invention for the preparation of a Art v 1 allergen is characterized by the following steps:
(a) cultivation of prokaryotic or eukaryotic host cells that contain a DNA (SEQ ID NO:1) coding for Art v 1 or DNA that has 60% sequence identity with this sequence, in a way that the Art v 1 allergen is expressed by the host cell
(b) isolation of the allergen Art v 1

This recombinant allergen can be glycosylated. For the method, a replicable prokaryotic or eukaryotic expression vector that contains the DNA molecules mentioned in step (a) of the method can be assigned. Such an expression vector is contained in the named host cells, which can be preferentially *Escherichia coli* or *Picchia pastoris* or of plant origin, such as tobacco (*Nicotiana*). In addition, a tobacco (*Nicotiana*) plant can comprise a eukaryotic expression vector comprising the DNA molecules of the invention.

The isolation of an authentic and complete cDNA clone that codes for Art v 1a (FIG. 1), the major allergen of mugwort pollen is shown. The letter a in Art v 1a signifies isoform a. In addition, two further clones were isolated that code for authentic and complete isoforms of Art v 1 as well, that are called Art v 1b and Art v 1c. The sequences of the two latter isoforms are shown in FIG. 2 and FIG. 3. The clones are complete in their 5' ends because they contain the start AUG codon in a typical eukaryotic context. The clones are complete in the 3' region because they contain 177–200 nucleotides after the stop codon, followed by the polyA$^+$-tail. The sequences outside the open reading frame are not shown in the figures. The alignments of the nucleotide and deduced amino acid sequences of Art v 1a, b and c are shown in FIGS. 4 and 5, respectively. The comparisons show that Art v 1 is a mixture of different isoforms that show relatively large sequence deviations from each other, both at the nucleotide and amino acid levels. These differences are even more pronounced when the non-translated upstream and downstream parts of the nucleotide sequence are also taken into account (not shown). The number of different isoforms and of nucleotide substitutions makes it very probable that we are dealing with a gene family. The gene family is certainly not species or genus-specific because a homologous sequence has been detected in sunflower (4). The sunflower protein (SF18) is expressed in epidermal anther cells possibly indicating a pollen-specific function and displays some similarity to the gamma-purothionin family.

DETAILED DESCRIPTION OF PREFERRED EMBODIMENTS

EXAMPLES

The isolation of the cDNA clone coding for Art v 1a was done in the following way:

A cDNA expression library in the phage lambda-ZAP II (Stratagene, La Jolla, Calif.; catalogue No. 237612) was prepared. The starting material was mugwort pollen mRNA. The cDNA library was screened immunologically with a serum pool of 20 patients that had been shown to recognize Art v 1 in patient blots. A clone was isolated that reacted positively with the serum pool and on repeated re-screening gave 100% immunopositive plaques. The immune reaction to this clone was relatively weak but clearly positive. The proof that this clone codes for Art v 1 was as done as follows:

The major allergen Art v 1 was extracted from mugwort pollen under very mild conditions, namely room temperature and extraction with water for 15–30 min under light shaking. This extract was further separated by preparative gel electrophoresis and the fractions were tested by immunoblots. FIG. 6*a* shows three fractions (F1, F2, and F3) that were free of Coomassie-stainable protein impurities and contained protein bands migrating at apparent Mr between 22 and 29 kDa. Occasionally, a dimeric band corresponding to about 50 kDa is also seen. FIG. 6*b* shows the patient blots of these fractions. It is obvious that that the fraction of highest Mr binds IgE from all three patients tested while the fraction of lowest Mr is only weakly recognized by patients' sera. FIG. 6*c* was obtained after staining the same blot with the Boehringer Mannheim glycoprotein detection kit (DIG glycan/protein double labeling kit, catalogue No. 1500783). It is clear that all three fractions consist of glycoprotein. All three fractions were analyzed by N-terminal Edman degradation and yielded identical N-terminal sequences which are underlined in FIGS. 1–3. Computer analysis of the deduced protein sequence in FIG. 1 according to Nielsen et al. (5) predicts Art v 1 has a typical N-terminal hydrophobic signal sequence that causes targeting to the endoplasmatic reticulum and the Golgi apparatus. The sequence after the start of the mature form of the protein predicted by this computer algorithm is identical with the N-terminal sequence found in the natural protein (underlined in FIGS. 1–3). A very similar N-terminal partial sequence was found previously by Matthiesen et al. (6). It can be concluded that Art v 1 is a secreted glycoprotein, whose N-terminus was created by removal of a typical ER signal sequence. The natural protein is heterogeneous due to differences in the degree of glycosylation and the fully glycosylated form (F3 in FIG. 6) binds IgE best.

The primary cDNA clone of Art v 1 a was used as a hybridization probe after labeling with $^{32}$P by the random priming method. The library described above was screened with this probe and two additional clones were obtained and termed Art v 1b and Art v 1c. The clones were analyzed by DNA sequencing. The sequences are shown in FIGS. 2 and 3.

*E. coli* was used to express the mature (short) form of the Art v 1a protein as a non-fusion recombinant protein after re-cloning the appropriate part of the cDNA in the expression system pMW172. It is well known that recombinant proteins expressed in *E. coli* display no postsynthetic modifications (with the possible exception of N-terminal methionine cleavage) and in particular, they do not contain sugars. The construction of the expression plasmid is shown in FIG. 7. The recombinant Art v 1a protein was enriched in the soluble fraction of the E. coli proteins. FIG. 8 shows immunoblots of the soluble fraction with 15 individual patients. The apparent Mr of the natural protein is about 27 kDa (FIG. 8, mugwort pollen) while the apparent Mr of the recombinant protein is about 18 kDa due to the absence of glycosylation. The theoretical Mr is 10.8 kDa indicating that the recombinant protein shows a very unusual electrophoretic mobility in the SDS polyacrylamide gel electrophoresis. It is clearly seen (FIG. 8, rArt v 1a) that 10 of the fifteen patients' IgE recognize the unglycosylated protein but patients also exist that do not recognize this form of the protein. Quite surprisingly, patients 3, 4 and 10 recognize the unglycosylated protein much better than the natural glycosylated form. The controls in FIG. 8 show that *E. coli* proteins are not or only weakly recognized by patients and by the secondary antibody. These weak bands can be seen in all three patient blots shown in FIG. 8.

To explain the experimental results presented in the last paragraph, the following hypothesis is put forward. It can be envisioned that the sugar moieties of Art v 1 are necessary to bring the protein backbone into its natural conformation so that the IgE of some patients can bind the epitopes created in this way. Some other epitopes on the other hand can be easily recognized by the patients' sera in the absence of sugar. Another less probable explanation for the above observations is that patients' sera that do not recognize the unglycosylated form, in fact recognize epitope(s) consisting of sugars.

Preliminary Characterization of the Sugar Moieties of the Natural Major Allergen of *Artemisia vulgaris*, Art v 1

The natural major allergen of *Artemisia vulgaris* was purified to homogeneity by the following methods:
1. Anion exchange chromatography on Sepharose Q (Pharmacia, Uppsala, Sweden) at pH=5.2 and
2. HPLC-gel filtration chromatography on TSK-gel G2000SW (Tosohaas, Stuttgart, Germany).

The material was homogeneous as judged by N-terminal protein sequence and amino acid analysis, but had a heterogeneous molecular weight due to different glycosylation patterns. The molecular weight was determined by MALDI-TOF mass spectrometry and showed two broad peaks with a mean molecular mass of 13.5 kDa and 15.5 kDa, respectively. The apparent molecular weight determined by SDS-PAGE, on the other hand, was 24 to 28 kDa, which can be taken as an indication for a very unusual protein structure or for a very unusual structure of the sugar moieties. The preliminary analysis of the sugars covalently-bound to the polypeptide chain by hydrolysis and HPLC showed that no N-glycosylation and very likely also no typical 0-glycosylation are present on the Art v 1 allergen. Rather, a previously described plant 0-glycosylation on hydroxyproline residues seems to be the case. Art v 1 is a proline-rich protein (20% proline) and is postsynthetically modified so that in the mature protein proline and hydroxyproline residues are present in a ratio of 4:6. Extensive studies with five different lectins (*Galanthus nivalis* agglutinin, *Sambucus nigra* agglutinin, *Maackia amurensis* agglutinin, Peanut agglutinin, and *Datura stramonium* agglutinin) that are specific for known N-glycans and O-glycans showed that these sugar structures are not present in the Art v 1 allergen. The role of this unusual protein structure and unusual sugar moieties on the formation of B-cell epitopes of this major allergen is presently being investigated. FIG. 8 gives the first hint that the sugar moieties might play an important role in the IgE recognition of the Art v 1 allergen.

REFERENCES

1. Charpin, J., Surinyach, R., and Frankland, A. W. (1974) Atlas of European Allergenic pollens. Sandoz, Paris.
2. Spieksma, F. T. M., Charpin, H., Nolard, N., and Stix, E. (1980) Clin. Allergy 10: 319–329.
3. Cornillon, J., Bernard, J-P., Gueho, E., and Touraine, R. (1972) Rev. Franc. Allergol. 12: 131–135.
4. Domon, C., Evrard, J. L., Herdenberger, F., Pillay, D. T. N., and Steinmetz, A. (1990) Plant Mol. Biol. 15: 643–646.
5. Nielsen, H., Engelbrecht, J., Brunak, S., and von Heijne, G. (1997) Prot. Eng. 10: 1–6.
6. Matthiesen, F., Ipsen, H., and Løwenstein, H. (1991) In: Allergenic pollen and pollinosis in Europe. pp 36–44. D'Amato, G., Spieksma, F. T. M., and Bonini, S. eds., Blackwell Scientific Publications, Cambridge.

What is claimed is:

1. A recombinant DNA molecule coding for the Art v 1a allergen comprising the amino acid sequence shown in SEQ ID NO.2, which recombinant molecule hybridizes to the nucleotide sequence of SEQ. NO.1 under stringent conditions, said stringent conditions comprising hybridizing in 1M NaCl at 60° C., and washing twice in 5×SSPE and 0.1% SDS at 50° C.

2. The recombinant DNA molecule according to claim 1, which comprises the nucleotide sequence of SEQ. ID NO.1.

3. The recombinant DNA molecule according to claim 1, which comprises a nucleotide sequence derived from the amino acid sequence of SEQ. ID NO.2 on the basis of the degeneration of the genetic code.

4. A recombinant DNA molecule coding for the Art v 1b or Art v 1c allergen comprising the amino acid sequence shown in SEQ ID NO.4 or 6, respectively, which recombinant molecule hybridizes to the nucleotide sequence of SEQ ID NO.3 or 5, respectively, under stringent conditions, said stringent conditions comprising hybridizing in 1M NaCl at 60° C., and washing twice in 5×SSPE and 0.1% SDS at 50° C.

5. The recombinant DNA molecule according to claim 4, which molecule comprises the nucleotide sequence shown in SEQ ID NO.3 or 5, respectively.

6. A method for producing the Art v 1 allergen, comprising the following steps:

(a) growing prokaryotic or eukeryotic host cell comprising the recombinant DNA molecule according to claim 2 so that the Art v. 1 allergen is expressed by the host cells; and (b) isolating the Art v 1 allergen.

7. The method according to claim 6, In which the allergen is glycosylated.

8. A process for preparing a recombinant DNA comprising hybridizing a first nucleic acid to a second nucleic acid consisting of the nucleotide sequence of SEQ ID NO.1, 3 or 5 under stringent hybridization conditions, said stringent conditions comprising hybridizing in 1M NaCl at 60° C., and washing twice in 5×SSPE and 0.1% SDS at 50° C., and isolating the nucleic acid that hybridizes the second nucleic acid.

9. A replication-capable prokaryotic or eukaryotic expression vector comprising the recombinant DNA molecule of claim 2.

10. A prokaryotic or eukaryotic host cell comprising the expression vector according to claim 9.

11. The host cell according to claim 10, which host cell is *Escherichia coli*.

12. The host cell according to claim 10, which host cell is *Pichia pastoris*.

13. The host cell according to claim 10, which host cell is of plant origin.

14. The host cell according to claim 13, which host cell is *Nicotiana*.

15. A *Nicotiana* plant comprising the eukaryotic expression vector according to claim 9.

16. A method for producing the Art v 1 allergen, comprising the following steps:
   (a) growing prokaryotic or eukaryotic host cell comprising the recombinant DNA molecule according to claim 1 so that the Art v 1 allergen is expressed by the host cells; and
   (b) isolating the Art v 1 allergen.

17. The method according to claim 16, in which the recombinant allergen is glycosylated.

18. A replication-capable prokaryotic or eukaryotic expression vector comprising the recombinant DNA molecule according to claim 1.

19. A prokaryotic or eukaryotic host cell comprising the expression vector according to claim 18.

20. The host cell according to claim 19, which host cell is *Escherichia coil*.

21. The host cell according to claim 19, which host cell is *Pichia pastoris*.

22. The host cell according to claim 19, which host cell is of plant origin.

23. The host cell according to claim 22, which host cell is *Nicotiana*.

24. A *Nicotiana* plant the eukaryotic expression vector according to claim 18.

* * * * *

SEQUENCE LISTING

<160> NUMBER OF SEQ ID NOS: 6

<210> SEQ ID NO 1
<211> LENGTH: 399
<212> TYPE: DNA
<213> ORGANISM: Artemisia vulgaris

<400> SEQUENCE: 1

```
atggcaaagt gttcatatgt tttctgtgcg gttcttctga ttttcatagt tgctatcgga      60
gaaatggagg ccgctggttc aaagttgtgt gaaaagacaa gcaagacgta ttcgggtaag     120
tgcgacaaca agaaatgtga caaaaagtgt atagagtggg agaaagcgca acatggtgct     180
tgtcacaaga gagaagccgg caaagaaagt tgcttttgct actttgactg ttccaaatcg     240
cctcctggag caacaccagc gcctcctggt gcagctcctc ccccagctgc tggcggctct     300
ccgtcacctc ccgctgatgg tggctcacca cctcctccag ctgatggtgg atctcctcct     360
gtagatggtg gctctccacc tcctccgtcc actcactaa                            399
```

<210> SEQ ID NO 2
<211> LENGTH: 132
<212> TYPE: PRT
<213> ORGANISM: Artemisia vulgaris

<400> SEQUENCE: 2

```
Met Ala Lys Cys Ser Tyr Val Phe Cys Ala Val Leu Leu Ile Phe Ile
 1               5                  10                  15

Val Ala Ile Gly Glu Met Glu Ala Ala Gly Ser Lys Leu Cys Glu Lys
            20                  25                  30

Thr Ser Lys Thr Tyr Ser Gly Lys Cys Asp Asn Lys Lys Cys Asp Lys
        35                  40                  45

Lys Cys Ile Glu Trp Glu Lys Ala Gln His Gly Ala Cys His Lys Arg
    50                  55                  60

Glu Ala Gly Lys Glu Ser Cys Phe Cys Tyr Phe Asp Cys Ser Lys Ser
65                  70                  75                  80

Pro Pro Gly Ala Thr Pro Ala Pro Pro Gly Ala Ala Pro Pro Pro Ala
                85                  90                  95
```

```
Ala Gly Gly Ser Pro Ser Pro Ala Asp Gly Gly Ser Pro Pro Pro
            100                 105                 110

Pro Ala Asp Gly Gly Ser Pro Val Asp Gly Gly Ser Pro Pro Pro
            115                 120                 125

Pro Ser Thr His
    130

<210> SEQ ID NO 3
<211> LENGTH: 399
<212> TYPE: DNA
<213> ORGANISM: Artemisia vulgaris

<400> SEQUENCE: 3
atggcgaggt gttcatatgt tttctgcgcg gttcttctga ttttcgtact tgctatcgga      60
gaaattgagg ccgctggttc aaagctgtgt gaaaagacaa gcaagacgta ttcgggtaag    120
tgcgacaaca agaaatgtga caaaaagtgt atagaatggg agaaagcaca acatggtgct    180
tgtcacaaga gagaagccgg taagaaaagt tgcttttgct actttgactg ttccaaatcg    240
cctcctggag cgacaccagc gcctcctgga gcatctcctc ccccagctgc tggcggctct    300
ccaccacctc cgccgatggg tggctcacca cctcctccag ctgatggtgg atctcctcct    360
gccgatggtg gctctccacc tcctccgtcc gctcactaa                           399

<210> SEQ ID NO 4
<211> LENGTH: 132
<212> TYPE: PRT
<213> ORGANISM: Artemisia vulgaris

<400> SEQUENCE: 4

Met Ala Arg Cys Ser Tyr Val Phe Cys Ala Val Leu Leu Ile Phe Val
 1               5                  10                  15

Leu Ala Ile Gly Glu Ile Glu Ala Ala Gly Ser Lys Leu Cys Glu Lys
            20                  25                  30

Thr Ser Lys Thr Tyr Ser Gly Lys Cys Asp Asn Lys Lys Cys Asp Lys
        35                  40                  45

Lys Cys Ile Glu Trp Glu Lys Ala Gln His Gly Ala Cys His Lys Arg
    50                  55                  60

Glu Ala Gly Lys Glu Ser Cys Phe Cys Tyr Phe Asp Cys Ser Lys Ser
65                  70                  75                  80

Pro Pro Gly Ala Thr Pro Ala Pro Pro Gly Ala Ser Pro Pro Pro Ala
                85                  90                  95

Ala Gly Gly Ser Pro Pro Pro Ala Asp Gly Gly Ser Pro Pro Pro
            100                 105                 110

Pro Ala Asp Gly Gly Ser Pro Ala Asp Gly Gly Ser Pro Pro Pro
            115                 120                 125

Pro Ser Ala His
    130

<210> SEQ ID NO 5
<211> LENGTH: 399
<212> TYPE: DNA
<213> ORGANISM: Artemisia vulgaris

<400> SEQUENCE: 5
atggcaaagt gttcatatgt tttctgtgcg gttcttctga ttttcatact tgctatcgga      60
gaaatagagg ccgctggttc aaagctgtgt gaaaagacaa gcaagacgta ttcaggtaag    120
tgcgacaaca agaaatgtga caaaaagtgt atagaatggg agaaagcaca acatggtgct    180
```

-continued

```
tgtcacaaga gagaagccgg taaagaaagt tgcttttgct actttgactg ttccaaatcg     240
cctcctggag cgacaccagc gcctcctgga gcatctcctc ccccagctgc tggcggctct     300
ccaccacctc ccgccgatgg tggctcacca cctcctccag ctgatggtgg atctcctcct     360
gccgatggtg gctctccacc tcctccgtcc gctcactaa                            399
```

<210> SEQ ID NO 6
<211> LENGTH: 132
<212> TYPE: PRT
<213> ORGANISM: Artemisia vulgaris

<400> SEQUENCE: 6

```
Met Ala Lys Cys Ser Tyr Val Phe Cys Ala Val Leu Leu Ile Phe Ile
 1               5                  10                  15

Leu Ala Ile Gly Glu Ile Glu Ala Ala Gly Ser Lys Leu Cys Glu Lys
                20                  25                  30

Thr Ser Lys Thr Tyr Ser Gly Lys Cys Asp Asn Lys Lys Cys Asp Lys
            35                  40                  45

Lys Cys Ile Glu Trp Glu Lys Ala Gln His Gly Ala Cys His Lys Arg
    50                  55                  60

Glu Ala Gly Lys Glu Ser Cys Phe Cys Tyr Phe Asp Cys Ser Lys Ser
65                  70                  75                  80

Pro Pro Gly Ala Thr Pro Ala Pro Pro Gly Ala Ser Pro Pro Pro Ala
                85                  90                  95

Ala Gly Gly Ser Pro Pro Pro Pro Ala Asp Gly Gly Ser Pro Pro Pro
               100                 105                 110

Pro Ala Asp Gly Gly Ser Pro Pro Ala Asp Gly Gly Ser Pro Pro Pro
               115                 120                 125

Pro Ser Ala His
           130
```